(12) United States Patent
Juvinall

(10) Patent No.: US 7,060,999 B2
(45) Date of Patent: Jun. 13, 2006

(54) APPARATUS AND METHOD FOR INSPECTING RIBBED CONTAINERS

(75) Inventor: John W. Juvinall, Ottawa Lake, MI (US)

(73) Assignee: Owens-Brockway Glass Container Inc., Toledo, OH (US)

( * ) Notice: Subject to any disclaimer, the term of this patent is extended or adjusted under 35 U.S.C. 154(b) by 19 days.

(21) Appl. No.: 10/889,545

(22) Filed: Jul. 9, 2004

(65) Prior Publication Data
US 2006/0006352 A1    Jan. 12, 2006

(51) Int. Cl.
G01N 21/88    (2006.01)
G01N 21/90    (2006.01)

(52) U.S. Cl. .................. 250/559.44; 250/559.45; 250/223 B; 356/239.4; 356/630

(58) Field of Classification Search ............ 250/223 B, 250/559.22–559.24, 559.27, 559.28, 559.37, 250/559.38, 559.44, 559.45; 356/630, 635, 356/428, 239.4, 240.1
See application file for complete search history.

(56) References Cited

U.S. PATENT DOCUMENTS

| | | |
|---|---|---|
| 3,529,169 A | 9/1970 | Heaney et al. |
| 3,601,616 A | 8/1971 | Katsumata |
| 3,907,438 A | 9/1975 | Holeman |
| 4,021,122 A | 5/1977 | Krenmayr |
| 4,208,130 A | 6/1980 | Saconney et al. |
| 4,368,641 A | 1/1983 | McLeod, Jr. |
| 4,672,200 A | 6/1987 | Claypool et al. |
| 4,751,386 A | 6/1988 | Gardner |
| 4,852,415 A | 8/1989 | Bogatzki et al. |
| 4,866,263 A | 9/1989 | Fukuchi |
| 5,059,031 A | 10/1991 | Hamel et al. |
| 5,291,271 A | 3/1994 | Juvinall et al. |
| 5,442,446 A | 8/1995 | Gerber et al. |
| 5,489,987 A | 2/1996 | Ringlien |
| 5,661,294 A | 8/1997 | Buchmann et al. |
| 5,747,822 A | 5/1998 | Sinclair et al. |
| 5,896,195 A | 4/1999 | Juvinall et al. |
| 5,900,945 A * | 5/1999 | Hinata et al. ............... 356/428 |
| 6,025,909 A | 2/2000 | Juvinall et al. |
| 6,025,910 A | 2/2000 | Lucas |
| 6,104,482 A | 8/2000 | Brower et al. |
| 6,175,107 B1 * | 1/2001 | Juvinall ................. 250/223 B |
| 6,184,988 B1 | 2/2001 | Ferrari |
| 6,211,952 B1 * | 4/2001 | Weiland et al. .......... 356/239.4 |
| 6,256,095 B1 | 7/2001 | Ringlien |
| 6,275,287 B1 | 8/2001 | Watanabe |

(Continued)

FOREIGN PATENT DOCUMENTS

EP    0320139 A2    11/1988

(Continued)

Primary Examiner—Stephone B. Allen
Assistant Examiner—Davienne Monbleau

(57) ABSTRACT

An apparatus for inspecting a container having a central axis and a sidewall with circumferentially extending external ribs. The apparatus includes a light source for directing a line-shaped light beam onto an external surface of the container, a light sensor disposed to receive reflected portions of the line-shaped beam, and an information processor coupled to the light sensor to determine a geometric characteristic of the sidewall as a function of the reflected light energy. The line-shaped light beam preferably has a long dimension parallel to the container axis, and sufficient length to illuminate at least one rib peak and at least one valley between the rib peaks. The sensor may be a linear array sensor that is particularly useful for measuring out-of-round, or an area array sensor for measuring out-of-round and sidewall thickness.

6 Claims, 2 Drawing Sheets

U.S. PATENT DOCUMENTS

| | | |
|---|---|---|
| 6,480,280 B1 | 11/2002 | Hinata |
| 6,529,627 B1 | 3/2003 | Callari et al. |
| 6,549,288 B1 | 4/2003 | Migdal et al. |
| 6,549,292 B1 * | 4/2003 | Schmidt et al. ............. 356/630 |

FOREIGN PATENT DOCUMENTS

| | | | |
|---|---|---|---|
| EP | 0337421 | A2 | 4/1989 |
| EP | 0343664 | A2 | 5/1989 |
| EP | 0343665 | A2 | 5/1989 |
| EP | 0344617 | A2 | 5/1989 |
| EP | 0456910 | A1 | 12/1990 |
| EP | 0483966 | A2 | 9/1991 |
| EP | 0620430 | A1 | 4/1994 |
| EP | 0 878 705 | A1 | 11/1998 |
| EP | 1 288 613 | A2 | 3/2003 |
| GB | 2135452 | A | 2/1984 |
| JP | 63228049 | A * | 9/1988 |
| JP | 09133640 | A * | 5/1997 |
| JP | 11248644 | A * | 9/1999 |
| JP | 2003194532 | A * | 7/2003 |

* cited by examiner

APPARATUS AND METHOD FOR INSPECTING RIBBED CONTAINERS

The present invention is directed to the inspection of containers, and more particularly to a method and apparatus for detecting commercial variations in ribbed containers.

BACKGROUND OF THE INVENTION

In the manufacture of glass articles, such as glass containers, various anomalies or variations can occur that affect the commercial acceptability of the containers. These anomalies, termed "commercial variations," can involve one or more of numerous attributes of the containers. For example, commercial variations can include dimensional characteristics of a container at the container sidewall, the bottom or bearing surface, the container finish, or at the container sealing surface; they can also include variations such as stones or checks within the container finish, the sidewall or the bottom. It is conventional practice to mold indicia on each container that is indicative of the mold of origin of the container for inspection and quality control purposes. Thus, it is often useful to provide inspection equipment capable of inspecting the containers for commercial variations, mold indicia or other features that warrant inspection. The term "inspection" is used in its broadest sense to encompass any optical, electro-optical, mechanical or electrical observation or engagement with the container to measure or determine a potentially variable characteristic, including but not necessarily limited to mold codes and commercial variations.

U.S. Pat. No. 5,291,271 discloses an apparatus for measuring the sidewall thickness of transparent containers, which includes a source for directing a light beam onto the outer surface of the container sidewall at an angle such that a portion of the light beam is reflected from the outer sidewall surface, and a portion is refracted onto the container sidewall, reflected from the inner sidewall surface and then re-emerges from the outer sidewall surface. A lens is disposed between a linear array light sensor and the container sidewall for focusing light energy reflected from the outer and inner sidewall surfaces onto the sensor. The lens has an image plane in which the sensor is disposed and an object plane co-linear with the light beam. An information processor is responsive to light energy incident on the sensor for determining wall thickness of the container between the inner and outer sidewall surfaces.

U.S. Pat. No. 6,256,095 discloses an apparatus for inspecting the sealing surface area of a container finish that includes a light source positioned to direct a collimated line-shaped light beam (i.e., having a length dimension many times a width dimension) onto the sealing surface area of a container. The line-shaped light beam at the container surface area has a long dimension orthogonal to the container axis, and a narrow dimension tangential to the container axis. A light sensor is disposed to receive portions of the line-shaped light beam reflected from the sealing surface area, and provides an electrical output signal that varies with height or level of the sealing surface area with respect to the light source and sensor. A lens system is disposed to direct onto the light sensor only light energy reflected from the container sealing surface area in planes parallel to the common plane of the container axis and the sensor. The lens system and sensor together comprise a full imaging system for light energy reflected from the sealing surface in planes parallel to the common plane of the container axis and its sensor, but which is substantially immune from stray reflections, including reflections from other points on the container, that are not parallel to this plane.

SUMMARY OF THE INVENTION

The present invention includes a number of aspects, which can be implemented separately from or, more preferably, in combination with each other.

According to one aspect of the invention, there is provided an apparatus for inspecting a container having a central axis and a sidewall with circumferentially extending external ribs. The apparatus preferably includes a light source for directing a line-shaped light beam onto an external surface of the container, a light sensor disposed to receive reflected portions of the line-shaped beam, and an information processor coupled to the light sensor to determine a geometric characteristic of the sidewall as a function of the reflected light energy. The line-shaped light beam preferably has a long dimension parallel to the container axis, and sufficient length to illuminate at least one rib peak and at least one valley between the rib peaks. The sensor may be a linear array sensor that is particularly useful for measuring out-of-round, or an area array sensor for measuring out-of-round and sidewall thickness.

According to another aspect of the invention, there is provided an inspection apparatus for inspecting a container having a central axis, a radius and a sidewall with at least one circumferentially extending rib. The apparatus generally includes a light source, a lens system, a light sensor and an information processor. The information processor utilizes an image formed on the light sensor by light emitted by the light source and refracted by the lens system light to determine at least one geometric characteristic of either the sidewall or a rib.

According to another aspect of the present invention, there is provided a method of inspecting a container sidewall that has at least one circumferentially extending rib. The method generally includes the steps of: (a) providing a light source for directing light onto the sidewall, (b) providing a lens system, (c) providing a light sensor for receiving light such that an image having a first image element is formed on the light sensor, (d) rotating the container about its axis, (e) monitoring the first image element as the container rotates, and (f) determining a geometric characteristic of either the container sidewall or the rib based on the first image element.

BRIEF DESCRIPTION OF THE DRAWINGS

The invention, together with additional objects, features, advantages and aspects thereof, will be best understood from the following description, the appended claims and the accompanying drawings, in which:

DETAILED DESCRIPTION OF PREFERRED EMBODIMENTS

Figure 1:
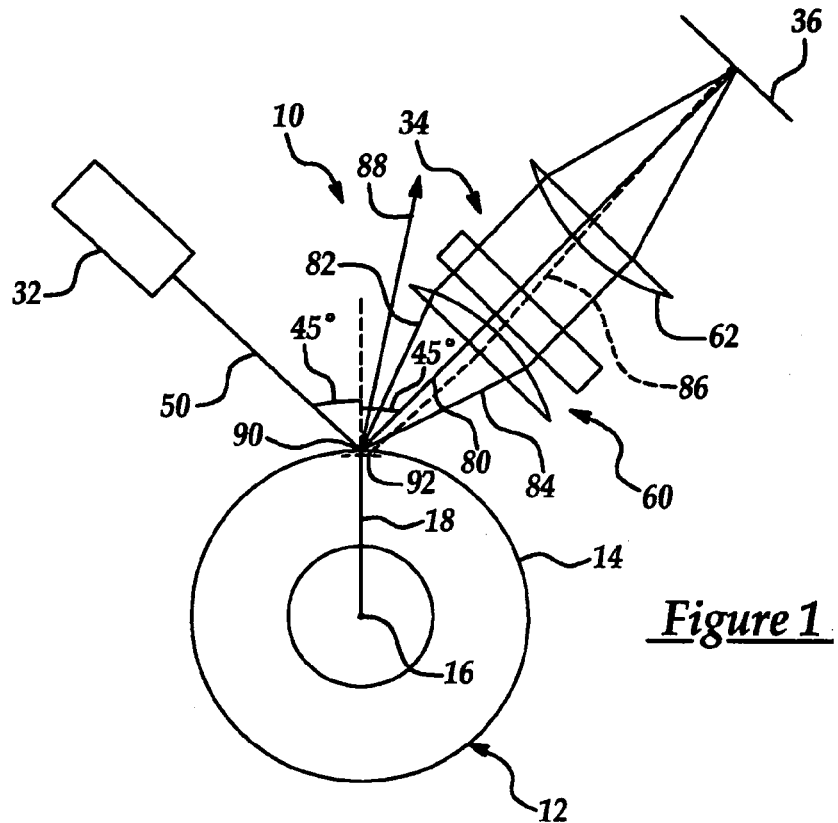
FIG. 1 is a plan schematic diagram showing a first embodiment of the container inspection apparatus of the present invention.
Figure 2:
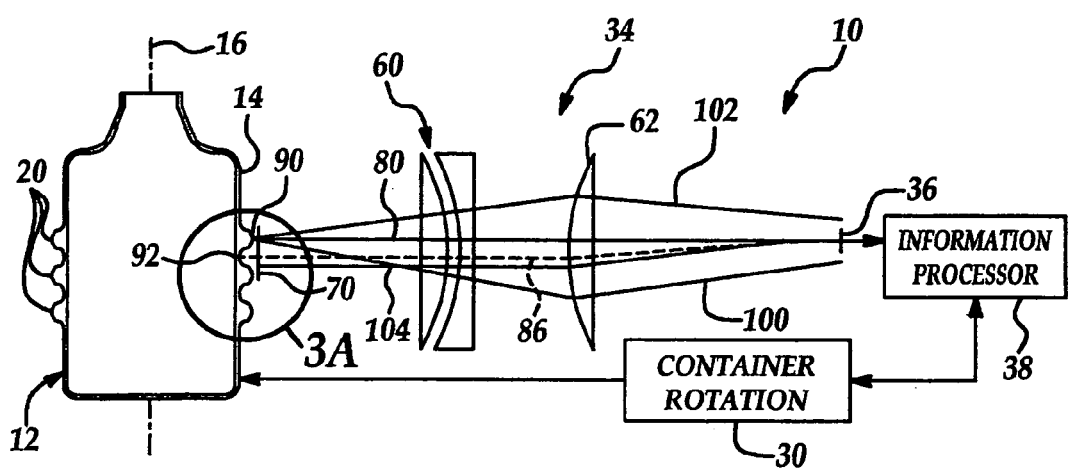
FIG. 2 is an elevational schematic diagram showing the container inspection apparatus of FIG. 1.

Referring to FIGS. 1 and 2, there are shown schematic diagrams of a first embodiment of a container inspection apparatus 10 used to detect commercial variations in a container 12, namely variations in the sidewall thickness and/or out-of-round or wobble of the container's ribbed sidewalls. Container 12 preferably is a transparent or a translucent glass container having a substantially cylindrical sidewall 14, a central axis 16 and a radius 18. The cylindrical sidewall further includes one or more circumferentially extending ribs 20, the size and shape of which vary by application. Inspection apparatus 10 can be part of a larger overall container inspection station and/or machine, or it can be a stand-alone inspection apparatus located along a conveyer or other container transportation system. In either case, container inspection apparatus 10 preferably includes a container rotation device 30 (FIG. 2), a light source 32 (FIG. 1), a lens system 34, a light sensor 36 and an information processor 38 (FIG. 2).

Container rotation device 30 preferably rotates container 12 around central axis 16 so that inspection apparatus 10 can inspect the container through at least one full rotation. The rotation device is coupled to information processor 38, and information processor 38 scans sensor 36 at equal angular increments of container rotation, or at equal time increments while the container is rotated at constant velocity. The information processor provides the rotation device with instructions as to when to begin rotating the container, how fast to rotate the container, how long to maintain rotation, etc.

Light source 32 emits an incident line-shaped light beam 50 that impinges upon sidewall 14 such that geometric characteristics of the sidewall and/or ribs, such as those pertaining to thickness and/or out-of-round, can be evaluated for commercial variations. The light source is coupled to and controlled by information processor 38, and preferably includes a laser diode for generating a light ray (one-dimensional), an internal lens arrangement for focusing the beam, and a line generator for transforming the ray into a line-shaped beam (two-dimensional). The light source directs incident line-shaped light beam 50, which is preferably a collimated beam of coherent light energy, onto sidewall 14 at an incidence angle, preferably of approximately 45° with respect to radius 18 (FIG. 1). As shown in FIGS. 1–3A, line-shaped beam 50 preferably has a long dimension parallel to container axis 16 and a short dimension tangential to the container axis. Of course, other suitable light sources and incident light patterns can be used as well.

Lens system 34 is located between container sidewall 14 and light sensor 36, and is used to collect and refract light that is reflected from the container sidewall such that it strikes the light sensor. Lens system 34 preferably is an anamorphic lens system that includes a cylindrical lens 60 positioned adjacent a spherical or a fresnel lens 62. Selection between a spherical lens and a fresnel lens is made, at least in part, by its focal length, which affects the position of light sensor 36 with respect to lens system 34. The lens system is designed to direct certain components of the light reflected from container sidewall 14 towards light sensor 36, while directing other components of the reflected light away from the light sensor. Lens system 34 will be subsequently described in greater detail.

Light sensor 36 is positioned near the focal point of lens system 34 such that it may receive light from the lens system and transmit electronic signals to information processor 38 that are representative of sidewall 14 and/or ribs 20. According to this embodiment, light sensor 36 includes a linear array sensor having a long dimension (FIG. 1) perpendicular to container axis 16 and a short dimension (FIG. 2) parallel to the container axis. Sensor 36 may be provided in a camera, such as a Dalsa Orion series camera, which can have associated focusing optics. Sensor 36 alternatively could be an area array sensor, in which only one line of CCD elements is scanned.

Information processor 38 is coupled to and communicates with various components of inspection apparatus 10, and analyzes geometrical characteristics of the sidewall and/or the ribs based upon information received from light sensor 36. Preferably, information processor 38 includes one or more inputs and/or outputs for communicating with container rotation device 30, light source 32 and light sensor 36, as well as numerous other electronic components. These components can include, but are not limited to, electronic memory devices, electronic processing devices, integrated circuits, peripheral components, etc., and can be part of inspection apparatus 10 or part of a larger inspection station or machine. Container rotation device 30, light source 32 and light sensor 36 preferably are all controlled by information processor 38.

In general operation, inspection apparatus 10 inspects geometric characteristics of container sidewall 14 and ribs 20 by analyzing light that has been emitted by the light source, reflected from the container sidewall, passed through the lens system, and received by the light sensor. Such inspection can uncover commercial variations, including those pertaining to sidewall thickness, rib thickness, sidewall out-of-round or wobble, and rib axial separation, to name but a few. Referring now to FIGS. 1–3A, light source 32 emits line-shaped light beam 50 that illuminates an axial section of container sidewall 14. The long, axial dimension of light beam 50 preferably is slightly longer than one cycle of ribs 20 such that at least one peak 72 and at least one valley 74 are illuminated. One advantage of inspection apparatus 10 is that the axial height of container 12, as well as the relative location of the ribs with respect to the inspection apparatus, is not critical. If during inspection the container is slightly moved in the axial direction, then light beam 50 will still strike at least one rib peak and one rib valley such that a proper inspection of the ribs can be performed. Of course, the long, axial dimension of light beam 50 could be elongated even further so that it illuminates an axial section of the sidewall that spans multiple ribs.

The incident light and the reflected light respectively include a nominal incident axis (aligned with beam 50) and a nominal reflection axis (aligned with beam 80); these are the axes of the incident light and the reflected light under ideal conditions, where a line tangent to the surface of the sidewall is perpendicular to container radius 18. The nominal incident axis and the nominal reflection axis preferably are angled at 45° with respect to radius 18, and preferably form an included angle of 90°. Furthermore, each of these nominal axes preferably lie in an imaginary horizontal plane that is perpendicular to central axis 16. Because reflected light beam 80 is not necessarily a single ray of light, although it could be, light beam 80 is generally "centered" on the horizontal plane described above. Thus, not all components of reflected light beam 80 may fall on the same horizontal plane, but the reflected light beam as a whole is centered upon a horizontal plane.

When line-shaped light beam 50 strikes the container sidewall, light can reflect from several different surfaces of the sidewall. First, there are those components of light seen in the horizontal plane shown in FIG. 1; second, there are those components of light seen in the vertical plane shown in FIGS. 2–3A. Referring now to FIG. 1, several exemplary light beams are shown that generally are centered on the horizontal plane, including reflected beams 80–88. Reflected beams 80–88 all reflect from the container sidewall at the same reflection position 90. When reflection position 90 is located on an angulated sidewall surface (line tangent is not perpendicular to radius 18), whether it be a rib peak, a rib valley or some other sidewall feature, it causes the light to be reflected at an angle other than 45°. This is the case with beams 82–84 and 88. As long as beams 82 and 84 reflect from an angulated surface that is approximately perpendicular to radius 18, lens system 34 will collect them and direct them toward light sensor 36, such that they strike the light sensor at the same place as nominal axis or beam 80. If, however, the light reflects off of the angulated sidewall surface at an angle that greatly diverges from nominal axis 80, such as with beam 88, then the reflected beam will not be collected by lens system 34 and will not strike light sensor 36.

Beam 86 originates from a reflection position 92 of the container sidewall surface that is perpendicular to radius 18, but is radially spaced from reflection position 90. Lens system 34 refracts beam 86 such that it strikes light sensor 36, but does so at a place slightly spaced from the place where nominal axis 80 and reflected beams 82–84 strike the sensor. The places at which the various beams strike light sensor 36 are referred to as "image positions". Thus, in the horizontal plane of FIG. 1, the combination of lens system 34 and light sensor 36 functions as a full imaging system. It should be noted that beams 80–84 all reflect from the container sidewall surface at the same reflection position 90, whether that point is located on a section of the surface that is perpendicular to radius 18 or is slightly angulated, and strike light sensor 36 at the same image position 94. In contrast, image position 96 of beam 86 is displaced from image position 94 of beams 80–84, because reflection position 92 is radially spaced from reflection position 90.

Figure 3B:
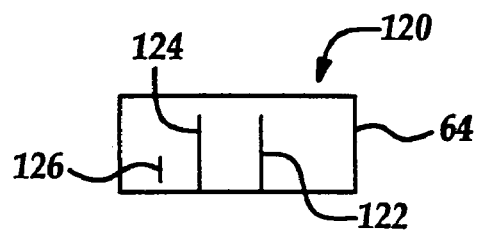
FIG. 3B is a blow-up view of an image produced by the container inspection apparatus of FIG. 1.
Figure 3A:
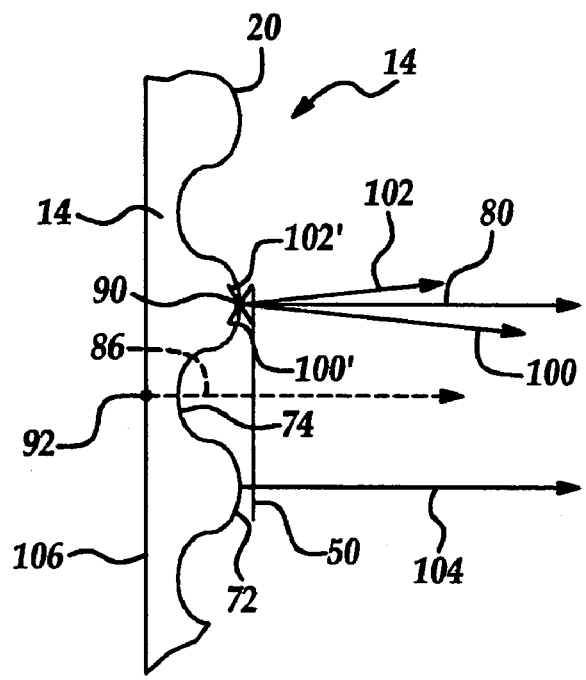
FIG. 3A is a blow-up of a section of the ribbed-neck of the container shown in FIG. 2.

Referring now to FIG. 2–3A, there are shown several exemplary light beams centered on an imaginary vertical plane, these beams include nominal reflection axis 80 and beam 86, which have already been discussed, as well as beams 100–104. Beams 100 and 102 strike container sidewall 14 at the same place, reflection position 90, as does nominal reflection axis 80. However, beams 100 and 102 impinge upon and reflect from angulated surfaces 100' and 102', respectively. This causes beams 100 and 102 to travel in non-parallel paths, with respect to nominal axis 80, which in turn causes them to be directed away from light sensor 36 by lens system 34. Accordingly, only those beams that strike reflection positions located on vertical or near-vertical surfaces of the container sidewall, such as peak 72 and valley 74, will end up striking light sensor 36. On the other hand, beam 104 strikes a vertical surface of the container sidewall, but does so at a reflection position that is axially spaced from position 90. Beam 104 extends in a path that is parallel to nominal reflection axis 80, which causes lens system 34 to direct beam 104 to light sensor 36 such that it strikes the sensor at the same image position 94 as does the nominal reflection axis.

Therefore, lens system 34 preferably acts as a telecentric lens system that focuses onto light sensor 36 only those light beams reflected from vertical or near-vertical surfaces of the container sidewall. This feature improves the inspection apparatus' insensitivity to axial movement of the container during rotation, such that small amounts of axial movement do not result in a failed inspection of an otherwise acceptable container. The apparatus of FIGS. 1–3A produces the image shown in FIG. 3B; that is, FIG. 3B shows the light pattern or image 120 formed on light sensor 36, which in this embodiment is a linear array sensor. Image 120 generally comprises three image elements 122–126, where the horizontal position of each image element relates to the distance between container sidewall 14 and inspection apparatus 10, and the vertical extent of each image element relates to the signal strength of each reflection. Lens system 34 compresses image 120 in the vertical direction such that image element 122 represents two overlapping image elements from two separate rib peaks (beams 80 and 104). This compression can be beneficial in that it reduces the amount of data being produced; a lower data-rate improves problems associated with a slow frame-rate. In this particular embodiment, image element 124 is representative of a single rib valley; however, if the container were axially shifted with respect to light line 50 such that two rib valleys 74 were illuminated, then image element 124 would represent two overlapping image elements. Image element 126 represents a reflection (beam 86) from an interior surface 106 of the container sidewall. Because light beam 86 passes through the thickness of the sidewall, its strength is attenuated and thus impinges upon light sensor 36 with a lesser signal strength than that of line images 122 and 124. The diminished signal strength produces a line image having a shorter vertical extent. Typically, those portions of the inner sidewall surface that are axially aligned with near-vertical sections on the outer sidewall surface are the most likely to reflect light to the sensor. It will sometimes be the case that no appreciable amount of light will reflect off of the inner container sidewall surface and be directed by lens system 34 to light sensor 36. In such a case, image 120 will only include lines 122 and 124.

Therefore, light sensor 36 generates a stream of data representative of image 120 which can be provided to information processor 38 in the form of a sensor output signal. The information processor preferably scans the light sensor at a constant predetermined interval, either a spatial or a temporal interval, to obtain and analyze this information for various geometric characteristics of container sidewall 14 and ribs 20, including the sidewall thickness, the radial separation of the ribs, the axial separation of the ribs, and any out-of-round conditions of the sidewall and/or the ribs. The thickness of the container sidewall between, for example, rib valley 74 and inner sidewall surface 106 is related to the horizontal distance between image elements 124 and 126. The thickness or radial separation of the ribs between rib peak 72 and rib valley 74 is related to the horizontal distance between image elements 122 and 124. The relative movement of each of the image elements 122, 124 and 126 is representative of out-of-round conditions of the rib peak 72, rib valley 74, and inner sidewall surface 106, respectively. Thus, if element 122 remains in approximately the same image position during rotation of container about its axis 16, then the circumferential surface of the rib peak is round, where if there is a certain degree of movement in the position of element 122, then the rib peak is out-of-round by a certain degree. Of course, other analysis could be performed with the data provided by light sensor 36. If a container is found to have an unacceptable commercial variation, then that container is flagged as a reject and is removed from the manufacturing process at a downstream station.

Figure 3C:
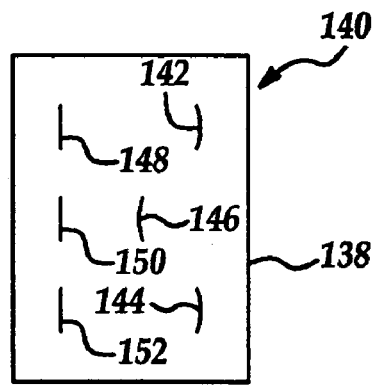
FIG. 3C is a blow-up view of an image produced by a second embodiment of the container inspection apparatus of the present invention.

According to another embodiment, an inspection apparatus is provided as before, only cylindrical lens 60 is removed and light sensor 36 includes an area array sensor 138 instead of a linear array sensor. With reference to FIG. 3C, removal of the cylindrical lens creates image 140, where the light beams are not compressed in the vertical direction. Put differently, parallel beams 80 and 104 strike light sensor 36 at different vertical positions and produce separate, non-overlapping image elements 142, 144, respectively, instead of being compressed on top of one another to form a element 122. Element 146 is representative of a reflection off of rib valley 74, and elements 148–152 represent reflections from inner surface 106 of the container sidewall. In the first embodiment, cylindrical lens 60 caused only that light reflected from vertical or near-vertical surfaces to impinge upon the light sensor; in this embodiment the lens system allows more light to strike the light sensor. Thus, image elements 142–146 have a slight curve to them, as they follow the curvature of the ribs more than that of image 120. One attribute of this embodiment is that it produces a more detailed image 140 of the container sidewall surface and ribs. For example, an inspection station of this embodiment could analyze the axial separation between adjacent rib peaks by monitoring the vertical distance between elements 142 and 144 as the container rotates. On the other hand, this embodiment produces a high volume of data or data-rate which can contribute to a slower frame-rate.

Figure 4:
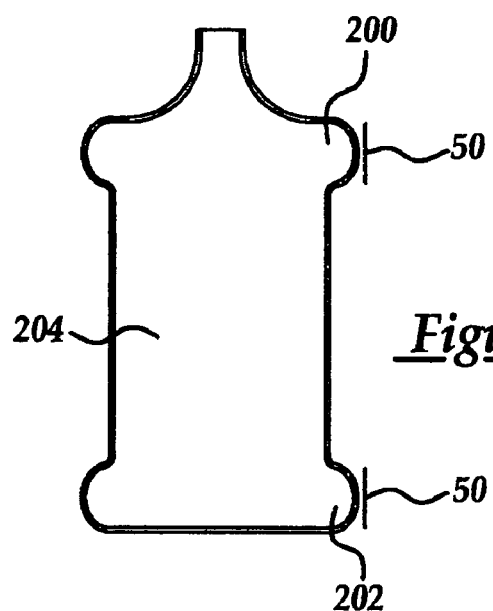
FIG. 4 is a schematic diagram that illustrates an alternative implementation of the invention.

FIG. 4 illustrates implementation of the invention for measuring the height and/or out-of-roundness of one or more ribs that appear as a shoulder bulge 200 and/or a heel bulge 202 on a container 204. FIG. 4 illustrates line-shaped beams 50 incident on the shoulder and/or heel bulge. The optics and electronics operate in the manner previously described in detail.

There have thus been disclosed an optical inspection apparatus and method, for inspecting a container sidewall and/or ribs, which fully satisfy all of the objects and aims previously set forth. Several alternatives and modifications have been described. Other alternatives and modifications will readily suggest themselves to persons of ordinary skill in the art. The majority of the discussion above pertains to the inspection of ribbed sidewall surfaces; however, non-ribbed or smooth sidewall surfaces could just as easily be inspected. In the case of a smooth sidewall surface the reflected light beam received by the light sensor would be a wide beam, having approximately the width of line-shaped light beam 50. The invention is intended to embrace all such alternatives and modifications as fall within the spirit and broad scope of the appended claims.

The invention claimed is:

1. Apparatus for inspecting a container having an axis and a sidewall with at least one circumferentially extending rib, which includes:

a light source for directing a line-shaped light beam onto an external surface of the container sidewall, with said line-shaped light beam having a long dimension parallel to said axis and of sufficient length to illuminate a peak of said at least one rib and at least one valley adjacent to said at least one rib, said line-shaped light beam being at an angle to said sidewall such that, at said at least one peak, a first portion of said light beam is reflected from an external surface of said sidewall and a second portion of said light beam is reflected from an internal surface of said sidewall, and at said valley a third portion of said light beam is reflected from an external surface of said sidewall and a fourth portion of said light beam is reflected from an internal surface of said sidewall, a light sensor disposed to receive said first, second, third and fourth portions reflected from said external and internal surfaces at said peak and said valley, and an information processor coupled to said light sensor to determine: (1) thickness of said sidewall at said peak as a function of separation between said first and second portions at said sensor, (2) thickness of said sidewall at said valley as a function of separation between said third and fourth portions at said sensor, and (3) height of said rib with respect to said valley as a function of separation between said first and third portions at said sensor.

2. The apparatus set forth in claim 1 including a device for rotating the container around said axis, and wherein said information processor is adapted to determine: (4) out-of-round of the container as a function of variations in position of incidence of at least one of said reflected beam portions on said sensor as the container is rotated.

3. The apparatus set forth in claim 1 including an anamorphic lens system disposed between the container and said sensor for directing onto said sensor only portions of said first, second, third and fourth portions that are reflected from surfaces at said peak and said valley that are perpendicular to a radius from said axis.

4. The apparatus set forth in claim 1 wherein said line-shaped light beam has a length parallel to said axis sufficient to illuminate at least two peaks and a valley between said at least two peaks on the container sidewall.

5. The apparatus set forth in claim 1 wherein said light sensor is a linear array sensor.

6. The apparatus set forth in claim 1 wherein said light sensor is an area array sensor.

* * * * *